United States Patent [19]
Frantzen

[11] Patent Number: 5,843,175
[45] Date of Patent: Dec. 1, 1998

[54] ENHANCED FLEXIBILITY SURGICAL STENT

[75] Inventor: John J. Frantzen, Copperopolis, Calif.

[73] Assignee: Global Therapeutics, Inc., Broomfield, Colo.

[21] Appl. No.: 874,975

[22] Filed: Jun. 13, 1997

[51] Int. Cl.$^6$ ................................................ A61F 2/06
[52] U.S. Cl. .................................................... 623/1
[58] Field of Search .................... 623/1, 12; 606/192, 606/194, 195, 198

[56] References Cited

U.S. PATENT DOCUMENTS

| | | | |
|---|---|---|---|
| 5,133,732 | 7/1992 | Wiktor | 606/195 |
| 5,139,480 | 8/1992 | Hickle et al. | 604/8 |
| 5,195,984 | 3/1993 | Schatz | 606/195 |
| 5,242,399 | 9/1993 | Lau et al. | 604/104 |
| 5,314,444 | 5/1994 | Gianturco | 606/195 |
| 5,421,955 | 6/1995 | Lau et al. | 216/48 |
| 5,425,739 | 6/1995 | Jessen | 606/155 |
| 5,441,515 | 8/1995 | Khosravi et al. | 606/194 |
| 5,443,477 | 8/1995 | Marin et al. | 606/198 |
| 5,449,373 | 9/1995 | Pinchasik et al. | 623/1 |
| 5,494,029 | 2/1996 | Lane et al. | 128/207.15 |
| 5,496,277 | 3/1996 | Termin et al. | 604/104 |
| 5,507,767 | 4/1996 | Meada et al. | 606/198 |
| 5,507,771 | 4/1996 | Gianturco | 606/198 |
| 5,514,154 | 5/1996 | Gaterud et al. | 623/1 |
| 5,531,741 | 7/1996 | Barbacci | 606/15 |
| 5,549,662 | 8/1996 | Fordenbacher | 623/1 |
| 5,569,295 | 10/1996 | Lam | 623/1 |
| 5,603,721 | 2/1997 | Lau et al. | 606/195 |
| 5,697,971 | 12/1997 | Fischell et al. | 623/1 |

FOREIGN PATENT DOCUMENTS 0 679 372 A2  11/1995  European Pat. Off. .

*Primary Examiner*—Mickey Yu
*Assistant Examiner*—John M. Black
*Attorney, Agent, or Firm*—Heisler & Associates

[57] ABSTRACT

A surgical stent (10) is provided which can be radially expanded away from a central axis (2) within a body lumen, such as an artery. The stent (10) is formed from a series of struts (20) circumscribing a cylindrical contour of the stent (10). Each strut (20) has a series of bends (30) formed therein with each bend including at least one trough (32) and at least one crest (36). Gaps (40) are provided between adjacent struts (20). Each gap (40) is spanned by an axial element such as a tie bar (50) or links (180). Each tie bar (50) attaches to adjacent struts (20) through troughs (32) so that when the stent (10) is radially expanded, the struts (20) are not drawn together, but rather maintain their position and the stent (10) hence maintains its axial length without contracting. Other elements such as the links (180) can be provided spanning the gaps (140) to provide enhanced flexibility for the surgical stent (110) including such links (180).

11 Claims, 10 Drawing Sheets

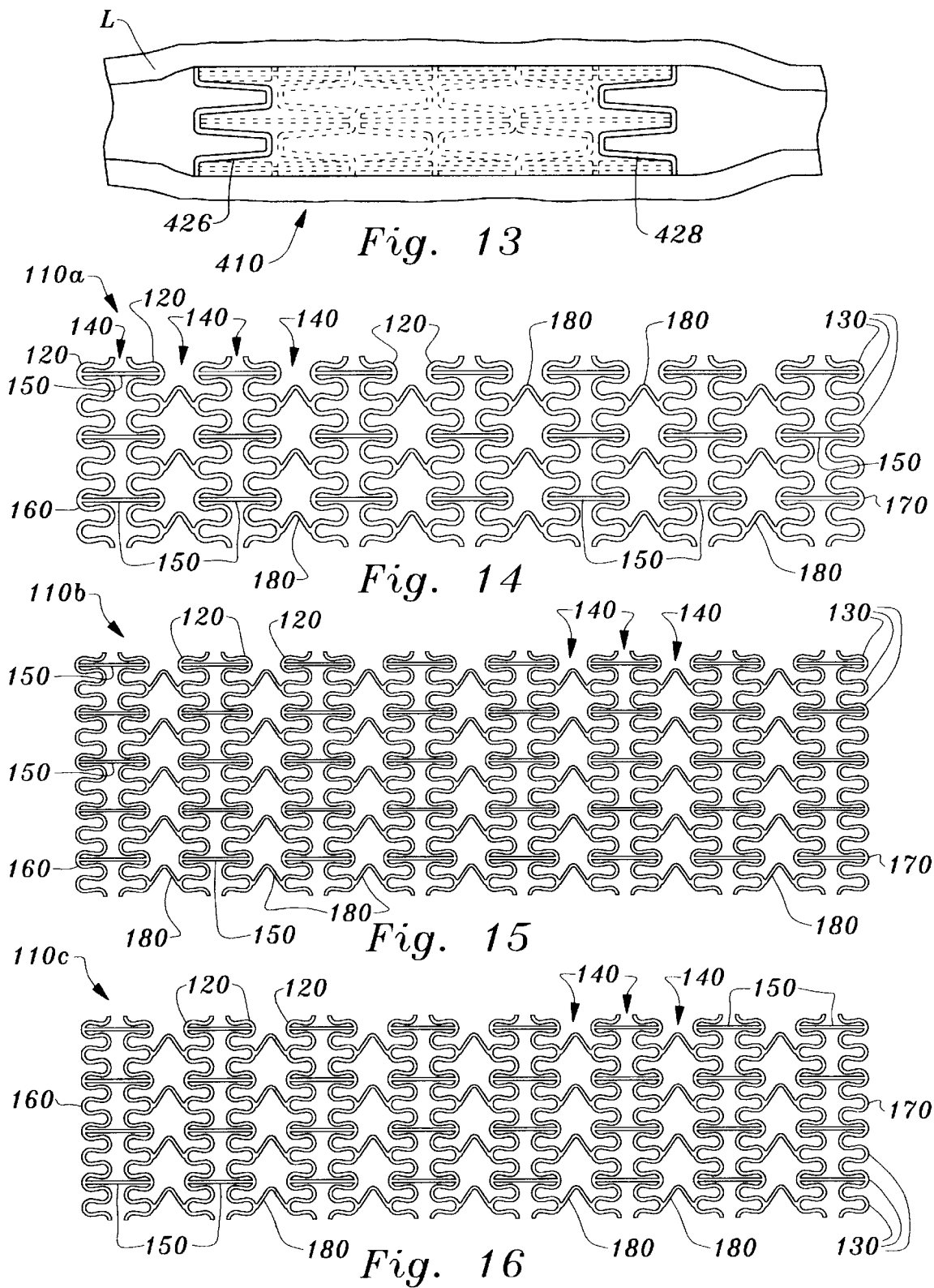

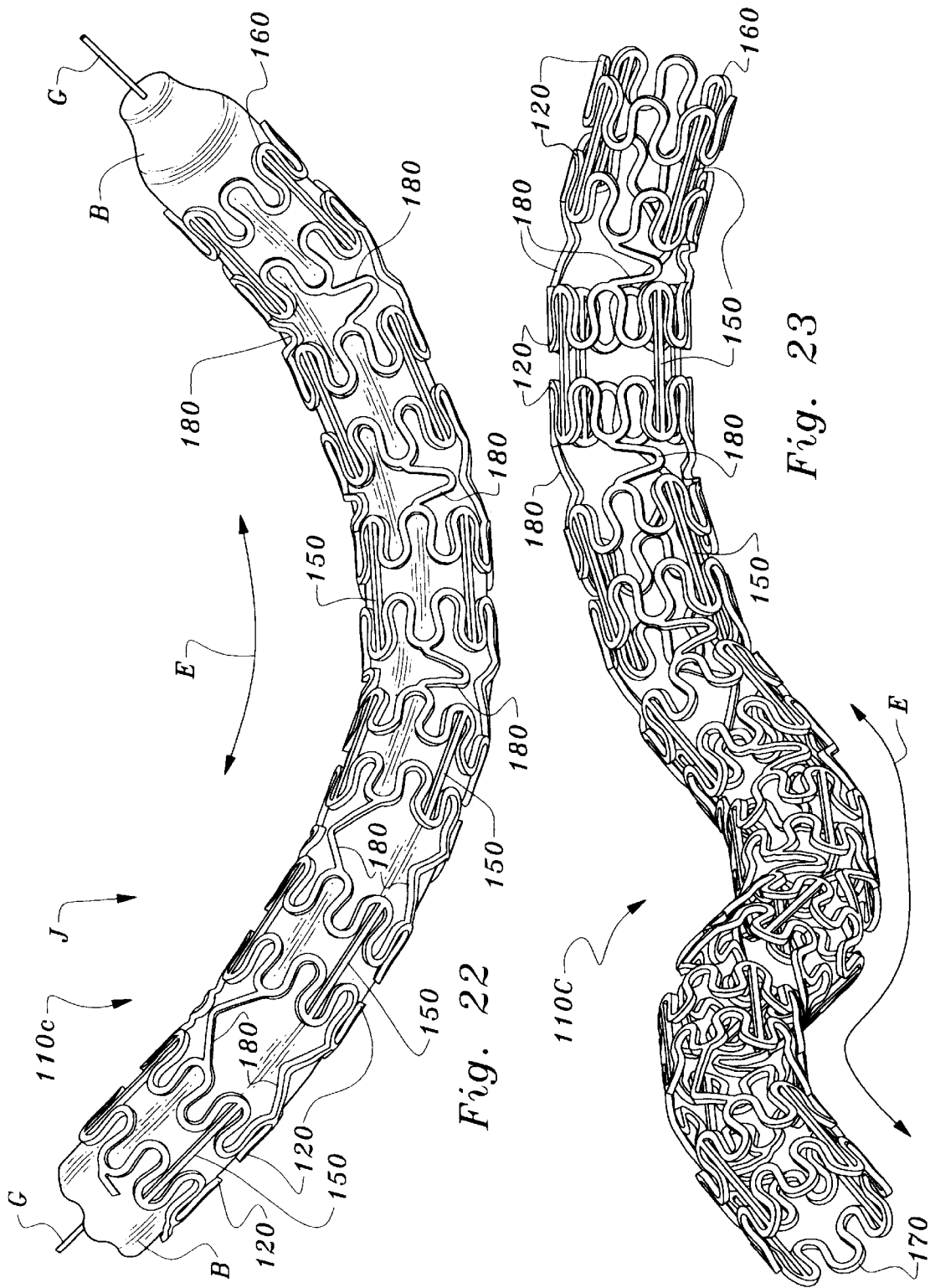

ENHANCED FLEXIBILITY SURGICAL STENT

FIELD OF THE INVENTION

The following invention relates to surgical stents of a generally cylindrical configuration which can be surgically implanted into a body lumen, such as an artery, and radially expanded. More specifically, this invention relates to radially expandable surgical stents which exhibit enhanced flexibility for passage through tortuous arterial pathways and other sharply curved body lumens.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a cylindrical stent which can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Each of these prior art stents suffer from a variety of drawbacks which make them less than ideal. For instance, many of these expandable stents are not particularly flexible and they have a central axis which remains substantially linear when the stents are not yet expanded. Such lack of flexibility makes the stent difficult to thread along arterial pathways for proper positioning within the body of the patient.

Some arterial pathways are not accessible by prior art surgical stents because of the tortuous nature of these arterial pathways. Without the availability of a stent having sufficient flexibility to navigate these tortuous arterial pathways, such arteries cannot be repaired using known prior art stents.

Another problem which is exhibited by each of these prior art stents is that when they are expanded radially, an axial length of these stents is decreased. Even the patent to Lau (U.S. Pat. No. 5,514,154), although it teaches a stent design which attempts to limit axial contraction, still exhibits some axial contraction, especially at one end thereof.

When a surgeon is positioning a stent within an artery or other body lumen, it is critical that the stent be positioned precisely where the surgeon desires the stent to be placed. A common occurrence with prior art stents is that the stent will be precisely located where desired before radial expansion and then when the stent is expanded, its axial contraction will cause the stent to not be finally located precisely where desired. Such a mis-location problem is compounded by the fact that most stents can only be easily expanded and not easily contracted once expansion has occurred.

Additionally, is is often difficult, even with state of the art medical imaging equipment, to accurately determine the location of a stent during implantation thereof within a body lumen. This difficulty in determining exactly what the position is of the stent compounds the problem of accurately locating the stent where desired. Accordingly, a need exists for a radially expandable stent which exhibits little or no axial contraction when radially expanded and which can be easily located by medical imaging equipment during the stent positioning process.

SUMMARY OF THE INVENTION

This invention provides a radially expandable stent which exhibits little or no contraction along an entire axial length thereof when the stent is expanded radially. The stent includes a series of struts which act as circumferential elements circumscribing the cylindrical contour of the stent. Each strut is aligned with a separate plane perpendicular to a central axis of the cylindrical contour of the stent and parallel to other planes of adjacent struts. The stent can have various different numbers of struts joined together to form the stent. However, at least two end struts are provided including a first end strut and a second end strut which define ends of the cylindrical contour of the stent. Intermediate struts are also typically provided between the two end struts.

Each of these struts exhibits a wave-like contour as they circumscribe the cylindrical contour of the stent. Thus, each strut has a series of bends which have troughs and crests alternating along the length of each strut. Each trough defines a portion of the strut which is most distant from adjacent struts and each crest defines a portion of the strut closest to adjacent struts. An amplitude of each strut, defined by the distance between the bottom of each trough and the top of each crest is modified when the stent is radially expanded so that the amplitude is generally decreased.

The end struts are attached to adjacent intermediate struts by tie bars which act as axial elements connecting the two adjacent struts together. Tie bars can also connect adjacent intermediate struts to each other. Each tie bar attaches to the struts adjacent thereto through a first junction on one extremity of the tie bar and a second junction on an opposite extremity of the tie bar. Both the first junction and the second junction are located within troughs of the struts. Thus, the tie bars span a gap between adjacent struts at a maximum width portion of the gap. Not all of the gaps are necessarily spanned by tie bar axial elements. Rather, separate intermediate circumferential elements can be attached to each other through links which connect to the intermediate elements at locations spaced away from the troughs thereof.

To maximize the flexibility of the stent and allow the stent to navigate highly curved tortuous arterial pathways, axial elements in the form of enhanced flexibility linking elements are provided spanning gaps between some of the struts. The gaps which are spanned by linking elements can be readily bent because the linking elements include a means to expand and contract axially. Each linking element has a left arm and a right arm connected together by an elbow. The elbow is sufficiently thin that it can bend somewhat, causing the left arm and right arm to flex toward and away from each other, in turn narrowing or expanding portions of the gap adjacent the flexible linking axial element. When the stent is flexed, some linking elements in a gap are contracted and some linking elements in the gap are expanded, causing the gap to have a variable width which is smaller on an inside of the curve of the stent and larger on an outside of the curve of the stent. As the stent moves through the curving arterial pathways, the linking axial elements can expand and contract as necessary to cause the gaps they span to flex and in turn causing the stent itself to flexibly adapt to a contour of the arterial pathway through which the stent is being passed.

Depending on the flexibility needs and strength needs for the stent, different numbers of troughs can be provided with tie bars attaching adjacent struts to each other. Also, a greater overall number of undulations and axial elements can be provided. If enhanced flexibility is desired, a fewer number of axial elements can be provided between adjacent struts or the arms of the linking axial elements can be lengthened. Also, the gaps in which the linking elements are located can be widened. The undulating contour of the struts can either be serpentine with the struts lacking flat surfaces but rather curving entirely along their length, or the struts can be formed from a series of linear sections including linear trough sections and linear crest sections joined together by linear inflection sections.

To enhance the visibility of the stent when viewed by various different medical imaging devices, the struts forming the first end and the second end of the stent can be formed from a radio-opaque material, such as gold, silver or platinum which will allow the first end and second end of the stent to be clearly visible through a medical imaging device during or after implantation of the stent within a body lumen of a patient.

OBJECTS OF THE INVENTION

Accordingly, a primary object of the present invention is to provide a radially expandable stent which does not contract axially when expanded radially.

Another object of the present invention is to provide a stent which exhibits sufficient flexibility to allow a central axis thereof to bend, especially when the stent is being threaded through arterial pathways within a patient.

Another object of the present invention is to provide a surgical stent which exhibits little or no axial contraction at ends thereof when expanded radially.

Another object of the present invention is to provide a surgical stent which has ends thereof formed from a radio-opaque material which can be easily viewed by a medical imaging device.

Another object of the present invention is to provide a surgical stent which is formed from a series of struts which form circumferential elements circumscribing a cylindrical contour of the stent, the individual struts joined together by tie bars which act as axial elements restraining the struts from contracting together when expanded radially.

Another object of the present invention is to provide a surgical stent which has a configuration which lends itself to manufacture from a variety of techniques including machining, photo-etching and other precision low cost techniques.

Another object of the present invention is to provide a surgical stent which has a configuration which exhibits the strength necessary to support a body lumen when implanted therein and radially expanded.

Another object of the present invention is to provide a surgical stent which can be located within a body lumen by a surgeon with a high degree of locational precision.

Another object of the present invention is to provide a surgical stent which is sufficiently flexible that it can be routed through tortuous arterial pathways leading up to a maximum number of potential stent implantation sites, including the diagonal arteries of the left anterior descending artery and the marginal arteries of the left circumflex artery and the right posterior lateral arteries of the heart.

Another object of the present invention is to provide a surgical stent which can be radially expanded to over twice its non-radially expanded diameter, does not substantially contract axially when radially expanded and which has sufficient flexibility to match a flexibility of a guide wire of a stent positioning catheter utilized to position and radially expand the stent.

Another object of the present invention is to provide a surgical stent which features axial elements in the form of flexible links which can expand and contract axially, causing gaps spanned by such flexible links to bend and imparting flexibility to the stent.

Other further objects of the present invention will become apparent from a careful reading of the included description and claims and from a review of the drawing figures.

BRIEF DESCRIPTION OF THE DRAWINGS

FIG. 13 is a front elevation view of the stent shown in FIGS. 11 and 12 as it would appear when viewed by a medical imaging device which more clearly discerns radio-opaque material than non-radio-opaque material, the lumen having been clearly outlined by a radio-opaque dye and portions of the stent formed from non-radio-opaque material shown in broken lines representing that they are only vaguely apparent.

FIG. 14 is a cylindrical projection of an alternative embodiment of the stent shown in FIGS. 5 and 6, where a greater number of axial linking elements are provided spanning gaps between struts of the stent.

FIG. 15 is a cylindrical projection of another alternative embodiment of that which is shown in FIGS. 5 and 6 where five links are provided spanning each gap and five tie bars are provided spanning each gap and where a greater number of bends are provided for each strut.

FIG. 16 is a cylindrical projection of another alternative embodiment of that which is shown in FIGS. 5 and 6 where four tie bars are provided spanning each gap and four links are provided spanning each gap and where a greater number of bends than that shown in FIGS. 5 and 6 are provided.

FIG. 22 is a perspective view of one of the stents of this invention in position upon a catheter with the catheter flexed as it would be when passing through a sharp curve in a body lumen prior to radial expansion of the stent.

FIG. 23 is a perspective view of one of the stents of this invention revealing how the stent can be flexed sufficiently to follow tortuous arterial pathways.

DESCRIPTION OF THE PREFERRED EMBODIMENT

Figure 1:
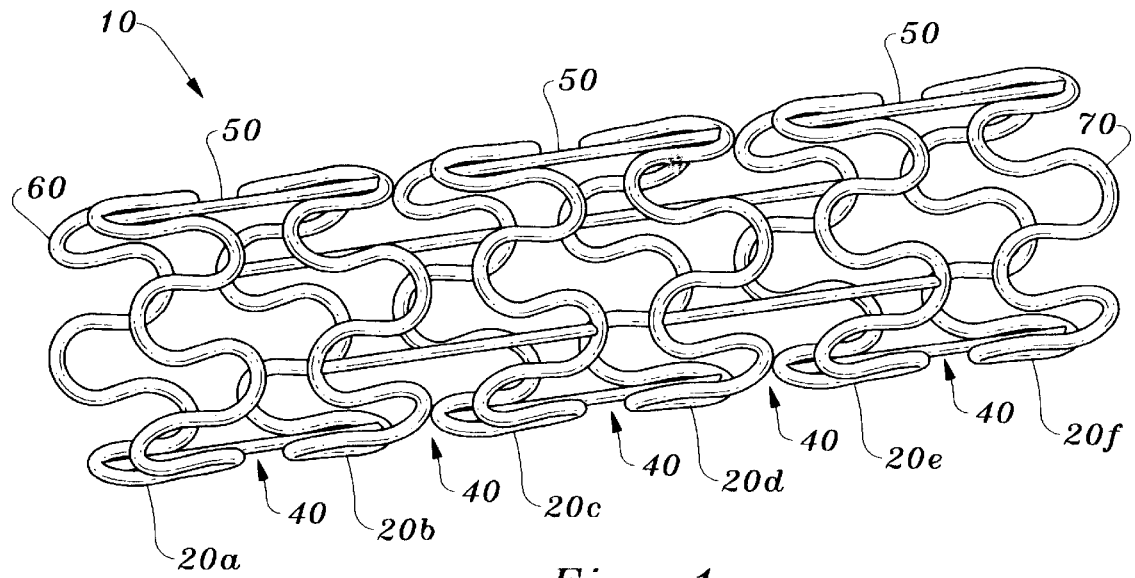
FIG. 1 is a perspective view of a preferred embodiment of the surgical stent of this invention before radial expansion occurs.
Figure 2:
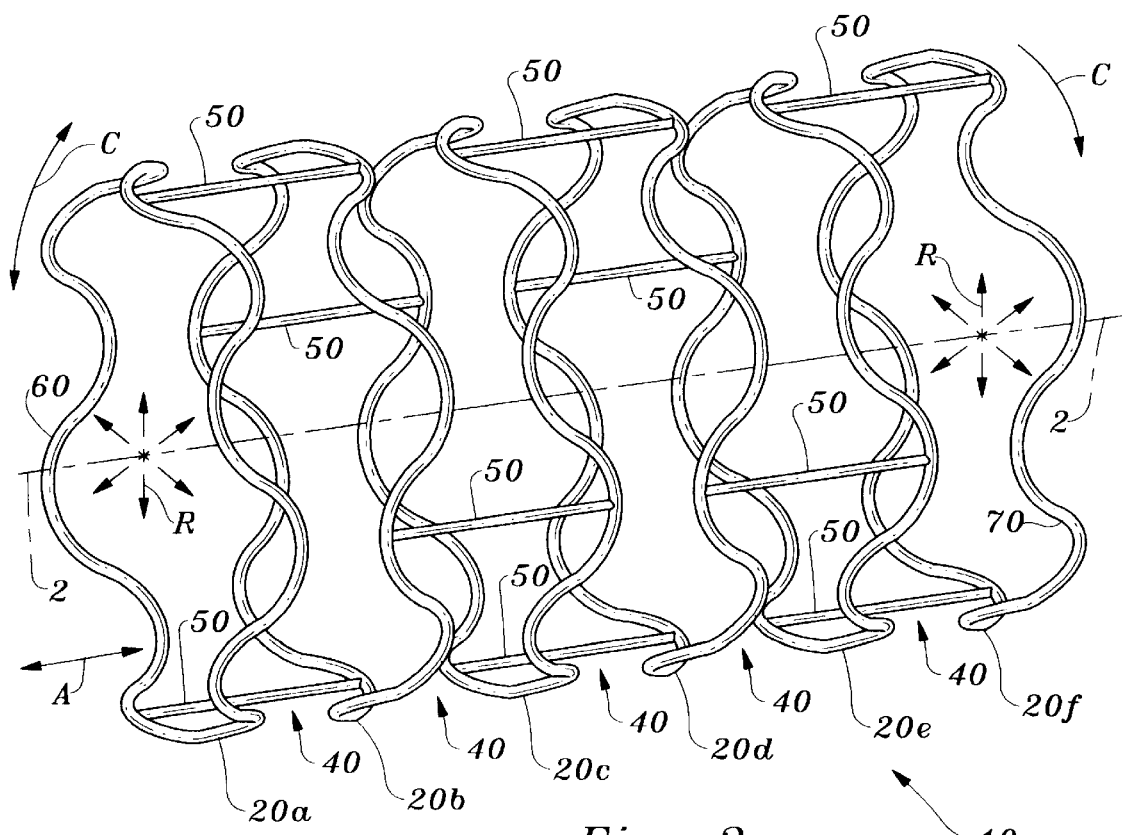
FIG. 2 is a perspective view of the stent which is shown in FIG. 1 after radial expansion has occurred.

Referring to the drawings, wherein like reference numerals represent like parts throughout the various drawing figures, reference numeral 10 is directed to a radially expandable axially non-contracting surgical stent (FIGS. 1 and 2). The stent 10 generally exhibits a cylindrical contour defined by a series of circumferential elements, referred to as struts 20, tied together by multiple axial elements, many of which are referred to as tie bars 50. The struts 20 are generally wave-like in form such that an amplitude 22 (FIG. 4) of the struts 20 can be decreased and a diameter of the struts 20 increased, as the diameter of the stent 10 is radially expanded.

Figure 3:
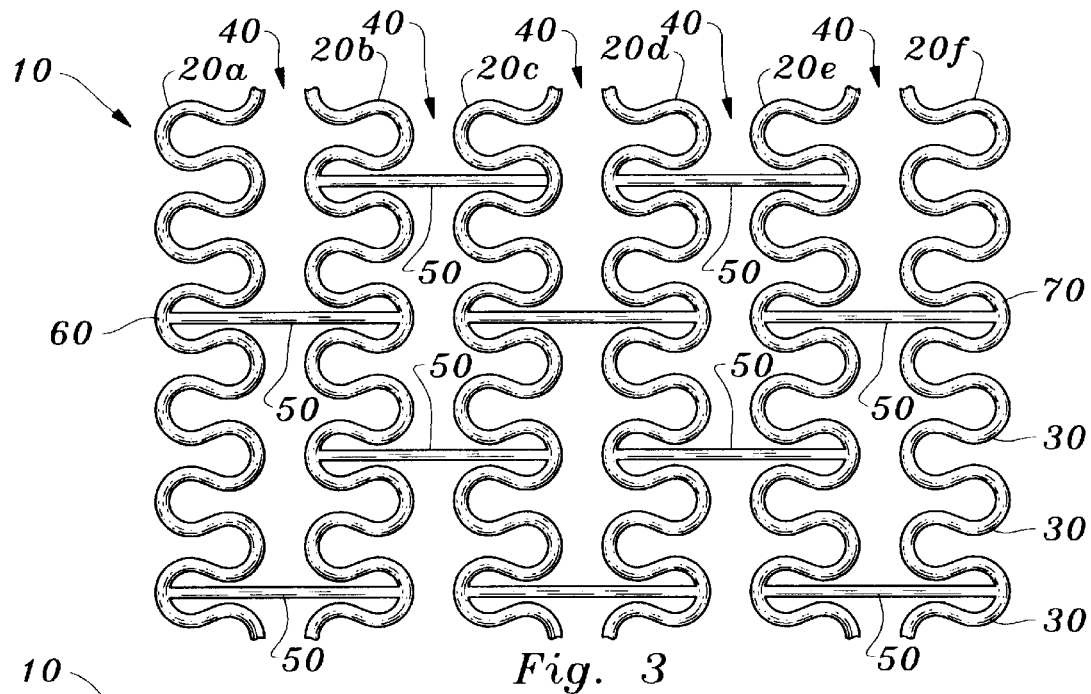
FIG. 3 is a top plan view of that which is shown in FIG. 1 after cylindrical projection of the stent onto a planar surface to reveal details of the configuration of the stent.

In essence, and with particular reference to FIGS. 1 and 2, the stent 10 includes the following basic features. A series of circumferential elements such as struts 20a, 20b, 20c, 20d, 20e, 20f are each oriented in a manner circumscribing the cylindrical contour of the stent 10. Each strut 20 includes a series of bends 30 (FIGS. 3 and 4) providing the strut 20 with its wave-like form. Each strut 20 is spaced from adjacent struts 20 by a gap 40 there between. A series of tie bars 50 extend between adjacent struts 20, and across the gap 40, connecting the adjacent struts 20 to each other. The tie bars 50 act as axial elements maintaining the axial position of the struts 20 during radial expansion of the stent 10 along arrow R (FIG. 2). The tie bars 50 are sufficiently flexible and spaced sufficiently apart from other tie bars 50 that the entire stent 10 can flex somewhat causing the central axis 2 to bend as the stent 10 is moved through arterial pathways or other body lumens before radial expansion of the stent 10.

More specifically, and with particular reference to FIGS. 1 through 4, details of the surgical stent 10 are specifically provided. Each strut 20 preferably is a thin elongate strand of material such as metal which is confined to lie substantially within a cylindrical contour forming the stent 10. Each strut 20 exhibits a wave-like contour having a constant amplitude 22 (FIG. 4) and wavelength 24 (FIG. 4) as it circumscribes the cylindrical contour of the stent 10. Each strut 20 thus has bends 30 therein which provide a series of alternating troughs 32 and crests 36. Between each adjacent trough 32 and crest 36 an inflection point 34 is provided which defines a transition between the trough 32 and the crest 36.

Whether a portion of a bend 30 is a trough 32 or a crest 36 is largely a matter of perspective. For consistency and with particular reference to FIG. 4, the trough 32 shall be identified as that portion of each bend 30 which is most distant from the adjacent strut 20 that the bend is facing, and the crest 36 is that portion of each bend 30 which is closest to the adjacent strut 20 that the bend 30 is facing. Each trough 32 and crest 36 is not a particular point on each bend 30, but rather is a region extending from one inflection point 34 to the next adjacent inflection point 34 along each strut 20. Whether a portion of a bend 30 is a trough 32 or a crest 36 also depends on the side of each bend 30 that is being analyzed. For example, a bend 30 spaced from a first end 60 and a second end 70 of the stent 10 can have a crest 36 on one side of the bend 30 closest to the first end 60 and a trough 32 on the other side of the same bend 30 closest to the second end 70.

Each inflection point 34 is the point at which the bend 30 transitions from curving in one direction (i.e. in a clockwise direction) to curving in an opposite direction (i.e. a counterclockwise direction). Each inflection point 34 is preferably a single point which occurs at the beginning and a middle of each wavelength 24 of each strut 20. However, the inflection point 34 can alternatively be a linear region between each crest 36 and each trough 32, rather than merely a point. Preferably, each strut 20 is aligned with adjacent struts 20 so that the troughs 32 of adjacent struts 20 are axially aligned with each other and the crests 36 of each strut 20 are axially aligned with each other.

A gap 40 is located between each pair of adjacent struts 20. Thus, end struts 20 such as the strut 20a adjacent the first end 60 and the strut 20f adjacent the second end 70 have only one gap 40 adjacent thereto and intermediate struts 20b, 20c, 20d, 20e have gaps 40 on either side. Preferably, each gap 40 defines a space between adjacent struts 20 which is not crossed by either strut 20 which is adjacent each gap 40. Rather, the tie bars 50, described in detail below, are provided to span the gaps 40.

Figure 4:
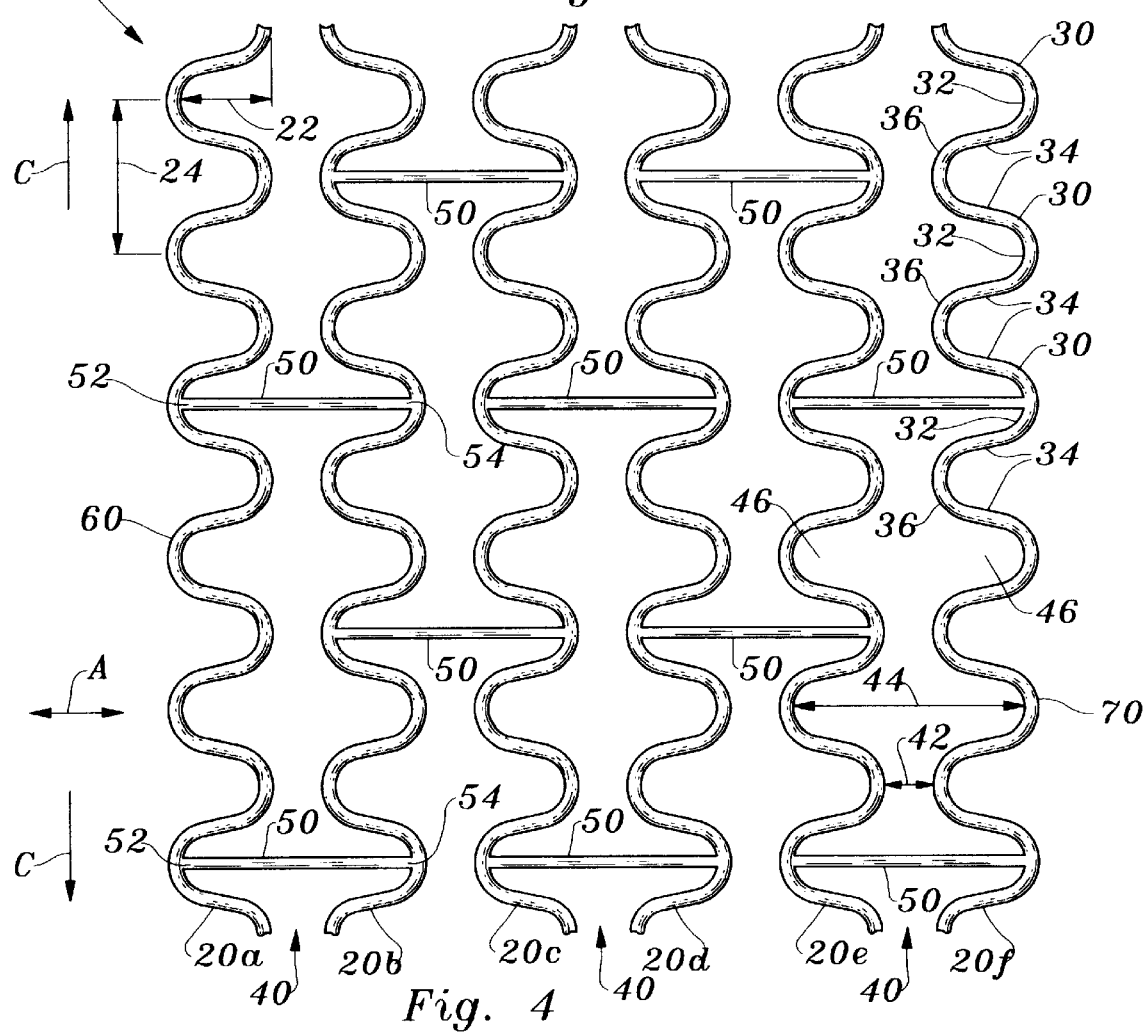
FIG. 4 is a top plan view of the stent which is shown in FIG. 2 after cylindrical projection of the stent onto a planar surface to reveal details of the configuration of the stent after radial expansion.

Each gap 40 has a width which varies depending on whether the gap 40 location is adjacent troughs 32 of adjacent struts 20 or crests 36 of adjacent struts 20. At locations on the gap 40 adjacent to the crests 36 of adjacent struts 20, a minimum width 42 in the gap 40 is defined (FIG. 4). At locations along the gap 40 adjacent the troughs 32 of adjacent struts 20, a maximum width 44 in the gap 40 is defined (FIG. 4). Each gap 40 thus exhibits an alternating pattern of minimums 42 and maximums 44 as the gap 40 circumscribes the cylindrical contour of the stent 10.

Each maximum 44 also defines a lateral slot 46 (FIG. 4) where the gap 40 extends a significant distance away from a central plane of the gap 40 and toward adjacent struts 20. The slot 46 has a contour which is defined by the configuration of the bends 30 of adjacent struts 20 and the radial expansion status of the stent 10 (i.e. before radial expansion along arrow R of FIG. 2 or after radial expansion). Preferably, before radial expansion along arrow R (FIG. 2), each slot 46 (FIG. 4) has a bulbous contour (FIG. 3) which mirrors a bulbous contour of the bends 30 such that the slot 46 first narrows and then expands as the slot 46 extends away from a center plane of the gap 40 and down into one of the troughs 32 in one of the bends 30 of an adjacent strut 20. After the stent 10 has been radially expanded (FIG. 4), the slots 46 lose this bulbous character and rather have a contour which tapers in width as the slots 46 extend away from a central plane of the gap 40.

By configuring the struts 20 to have this characteristic of bends 30 with a bulbous contour, providing the slots 46 with a narrowing and then expanding width, the struts 20 are allowed to expand further radially, along arrow R. This allows the stent 10 to extend to a greater length circumferentially, along arrow C (FIGS. 2 and 4), maximizing radial expandability thereof. This bulbous contour of the slots 46 also tends to allow the amplitude 22 (FIG. 4) of the struts 20 to remain unchanged during initial expansion of the stent 10 radially. Only after significant radial expansion and circumferential elongation does the amplitude 22 of the struts 20 begin to significantly decrease.

At least one tie bar 50 is oriented within each gap 40. The tie bar 50 is preferably a thin elongate structure having a first extremity spaced from a second extremity. The first extremity attaches to a first adjacent strut 20 at a first junction 52 and the second extremity attaches to a second adjacent strut 20 at a second junction 54. The first junction 52 and second junction 54 are both preferably located within troughs 32 of the struts 20 which are adjacent the gap 40 that is spanned by the tie bar 50.

To prevent axial contraction along arrow A (FIG. 2) during radial expansion of the stent 10, it is important that at least the extremities of the tie bar 50 which connect to end struts 20a, 20f adjacent the first end 60 and the second end 70 attach to troughs 32 of the end struts 20a, 20f. The second extremities of the tie bar 50 which connect to intermediate struts 20 spaced from the first end 60 and the second end 70 can either be attached within troughs 32 or crests 36.

With at least one tie bar 50 in place across each gap 40 and with the junctions 52, 54 located in troughs 32, the length of the slots 46 in the gap 40 are maintained. Thus, when the stent 10 is radially expanded along arrow R to the point where the amplitude 22 of the struts 20 adjacent each gap 40 begins to decrease, the struts 20 adjacent each gap 40 are not contracted together. Rather, the minimums 42 in the gaps 40 are enlarged and the struts 20, and particularly the end struts 20a, 20f maintain their position. Hence, no axial contraction along arrow A occurs.

Of primary importance in configuring the stent 10 is that gaps 40 adjacent the first end 60 and second end 70 be spanned by tie bars 50 which attach within troughs 32 in the struts 20a, 20f defining the first end 60 and the second end 70. Additionally, the other tie bars 50 between intermediate struts 20b, 20c, 20d, 20e can either be located in troughs 32 or at crests 36. However, the tie bars 50 between adjacent intermediate struts 20b, 20c, 20d, 20e should attach to at least an equal number of troughs 32 and crests 36 if not a greater number of roughs 32, as shown in FIGS. 1–4 where tie bars 50 only attach to troughs 32.

It has been determined from experience that the thin cross sections of the tie bars 50 cause the tie bars 50 to bend somewhat in many cases. Thus, it is beneficial to have a greater number of gaps 40 spanned by tie bars 50 which connect to adjacent struts 20 at troughs 32 thereof than tie bars 50 which attach to crests 36 thereof, to compensate for the possibility of flexing of the tie bars 50.

Preferably, each gap 40 is provided with tie bars 50 which extend from troughs 34 of each adjacent strut 20. While in theory such a configuration could actually cause the stent 10 to expand axially along arrow A when expanded radially along arrow R, the tie bars 50 bend somewhat when located within a body lumen and hence are slightly shortened, causing the stent 10 to in reality remain substantially the same axial length as before expansion, with only the slight possibility of a minimal amount of either contraction or expansion. For reference, it is noted that even so called non-contracting stents, such as the expandable stent taught by Lau (U.S. Pat. No. 5,514,154), can contract as much as one half of the amplitude of circumferential elements forming such prior art stents. This contraction of prior art stents such as that taught by Lau particularly occurs at ends of the stents where axial elements join circumferential elements at crests in the circumferential elements.

The material forming the struts 20 and other elements of the stent 10 are preferably made of a stainless steel having a sufficiently minimal cross section that the struts 20 can be easily loaded with radial force, such as along arrow R (FIG. 2), to a point exceeding the elastic limit of the material forming the struts 20. When such a radial force is applied, the material forming the struts 20 is plastically deformed, causing the struts 20 to expand radially, elongate circumferentially and contract in amplitude. Such deformation of the material forming the struts 20 could in theory occur until the struts 20 were deformed into the shape of a circle before additional deformation would eventually cause failure of the struts 20 in tension.

In practice however, the stent 10 is provided with overall structural strength by not expanding the stent 10 to its maximum possible amount, but rather to a point where the struts 20 still exhibit a wave-like appearance with the amplitude only slightly decreased and the wave length of the struts 20 magnified by a similar amount to the amount of magnification in the circumferential length of each strut 20. Although the struts 20 have undergone plastic deformation, the ultimate strength of the material forming the struts 20 has not been exceeded. Thus, the material still exhibits similar characteristics as far as strength is concerned and can provide the desired function of supporting a body lumen in its expanded configuration.

It is noted that stainless steel has a yield strength of between 40,000 and 75,000 pounds per square inch and an ultimate strength of between 90,000 and 125,000 pounds per square inch. Thus, it is relatively straight forward to provide sufficient radial force on the stent 10 to cause the material forming the struts 20 to have its yield strength exceeded but to not have its ultimate strength exceeded. This is especially true in that the struts 20 are actually "bending" and not "stretching" during the radial expansion process. Techniques for expanding stents such as the stent 10 are well known in the art. One such technique involves placing an expandable balloon within the stent which can be filled with air or other fluid, causing the balloon to elastically expand and exert a radial force on the stent. Specific details of such expansion techniques are articulated in the patents cited in the background of the invention and are incorporated herein by reference.

As an alternative to the surgical stent 10 of the preferred embodiment, a surgical stent 110 (FIGS. 5 and 6) is provided featuring links 180 spanning certain of the portions of the stent 110. The stent 110 is similar in configuration to the stent 10 of the preferred embodiment except as specifically identified below. Thus, the stent 110 includes struts 120 which provide circumferential elements for the stent 110 with bends 130 similar to the bends 30 in the struts 20 of the preferred embodiment and gaps 140 between adjacent struts 120. Each bend 130 includes a series of alternating troughs 132 and crests 136. Tie bars 150 similar to the tie bars 50 of the preferred embodiment are interposed across some of the gaps 140, while other gaps 140 are provided with the links 180. Preferably, the gaps 140 adjacent the first end 160 and the second end 170 are provided with tie bars 150 therein. In addition, these tie bars 150 are preferably oriented between troughs 132 of adjacent struts 120. Other gaps 140 spaced away from the first end 160 and second end 170 can either include tie bars 150 or links 180.

Each link 180 is a thin elongate structure having a left end 182 (FIG. 6), a right end 184 and an elbow 186 located medially between the left end 182 and the right end 184. Thus, the link 180 is provided with a left arm 187 extending from the left end 182 to the elbow 186 and a right arm 188 extending from the right end 184 to the elbow 186. Preferably, the elbow 186 causes the left arm 187 to be perpendicular to the right arm 188. The elbow 186 provides a particular location where the left arm 187 and right arm 188 of each link 180 can flex toward or away from each other about arrow F (FIG. 6) in a manner facilitating flexibility for the entire stent 110 when being threaded through arterial pathways.

The links 180 are preferably oriented at minimums 142 in the gap 140 in which the links 180 are located. Preferably, gaps 140 having the links 180 located therein alternate with gaps 140 having the tie bars 150 located therein and do not include gaps 140 adjacent the first end 160 and second end 170. When the stent 110 is expanded radially, and an amplitude of the bends 130 and the struts 120 is decreased, the links 180 will hold crests 136 of adjacent struts 120 together across the gaps 140. This will tend to have a contraction effect on the stent 110. However, the tie bars 150 being interposed between troughs 132 and adjacent struts 120 will tend to have an expanding effect on the stent 110. The net result of the tie bars 150 providing an axially expanding effect and the links 180 providing an axially contracting effect is that the stent 110 is provided with no or minimal net contraction when the stent 110 is expanded radially.

Preferably, the gaps 140 having tie bars 150 therein are provided with three tie bars 150 and the struts 120 are provided with six troughs 132 and six crests 136 such that only half of the possible tie bar 150 locations are utilized. Preferably, the gaps 140 fitted with links 180 include only two links 180 therein. Thus, four minimums 142 are left vacant. The locations of the links 180 are preferably circumferentially offset with the locations of the tie bars 150 to further enhance flexibility of the stent 110. Other stent designs similar to the surgical stent 110 featuring links 180 are shown in detail in FIGS. 14–23 with further details of such stents which enhance their flexibility further explained.

Figure 7:
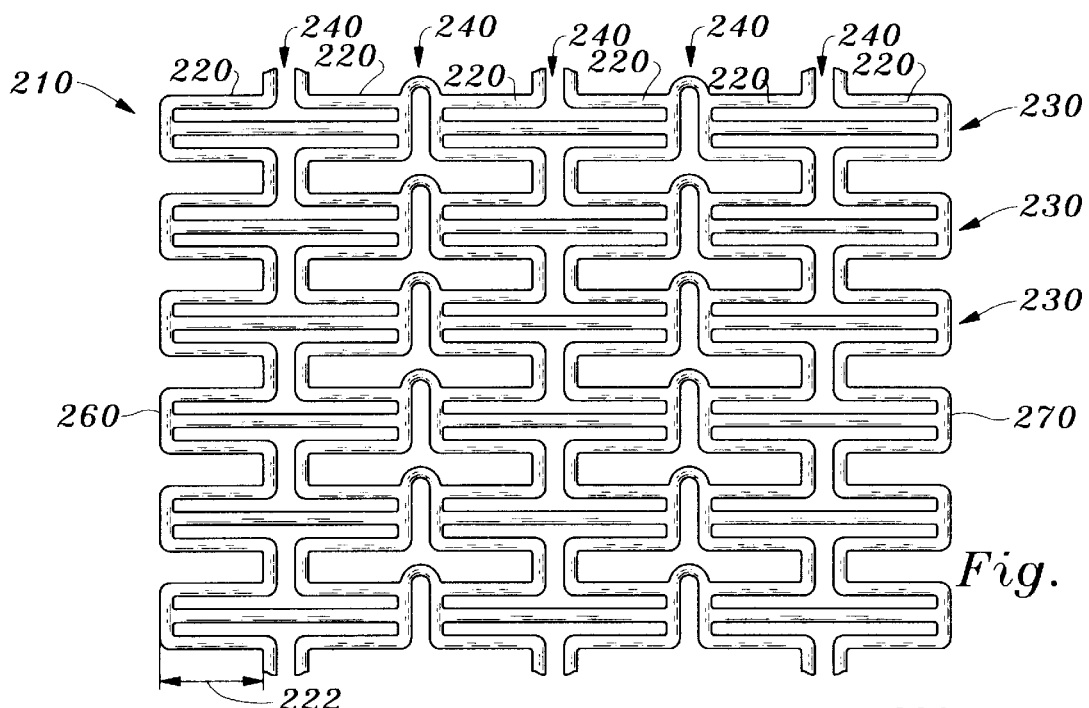
FIG. 7 is a top plan view of a stent forming a second alternative embodiment of that which is shown in FIG. 3, before radial expansion.
Figure 8:
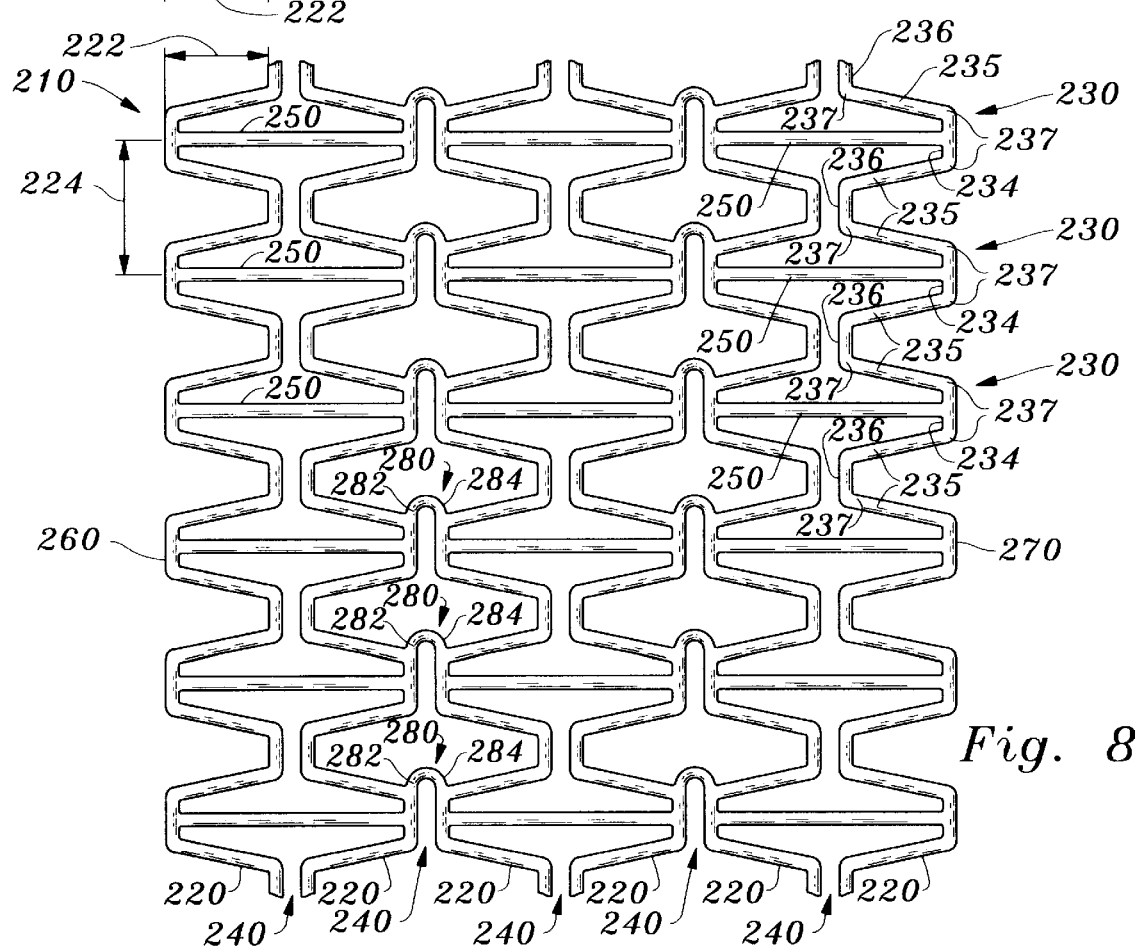
FIG. 8 is a top plan view of the stent which is shown in FIG. 7 after radial expansion has occurred.

With particular reference to FIGS. 7 and 8, details of a second alternative embodiment of the stent 10 featuring links and struts formed of individual linear segments is provided. Such a stent 210 still exhibits a cylindrical contour defined by a plurality of struts 220. Only those details of this stent 210 which differ from details of the stent 10 of the preferred embodiment will be provided in detail below. Each of the struts 220 has a wave-like appearance with a series of bends 230 located therein. However, each bend 230 is provided with a flat trough 234 (FIG. 8) parallel to and axially spaced from a plurality of flat crests 236. Each flat trough 234 and flat crest 236 is preferably oriented within a plane perpendicular to the central axis (see the central axis 2 of FIG. 2) of the stent 210.

Each flat trough 234 is connected to adjacent flat crests 236 by inflection legs 235. Each inflection leg 235 is preferably linear and is non-parallel with either the flat trough 234 or the flat crest 236. Corners 237 are provided at transitions between ends of the inflection legs 235 and adjacent flat troughs 234 and flat crests 236. The stent 210 expands radially in a similar manner to the stent 10 of the preferred embodiment except that the struts 220 are modified from a somewhat rectangular configuration for the bends 230 to a trapezoidal configuration for the bends 230. The amplitude 222 of the struts 220 is decreased when radial expansion occurs and the wave length 224 of the struts 220 is increased when radial expansion occurs in a manner similar to that exhibited by the stent 10 of the preferred embodiment.

Gaps 240 are oriented between adjacent struts 220 in the stent 210. Tie bars 250 are provided between flat troughs 234 in adjacent struts 220 and spanning the gaps 240. Such tie bars 250 are preferably located at the gaps 240 adjacent a first end 260 and a second end 270 and are optional at other gaps 240 in the stent 210.

As an alternative to the tie bars 250, the gaps 240 can be spanned by arched links 280 (FIG. 8). Preferably, each arched link 280 has a left end 282 spaced from a right end 284 and is bowed between the left end 282 and the right end 284. Preferably, the arched links 280 are interposed between adjacent flat crests 236 of struts 220 adjacent the gap 240 spanned by the arched link 280. The arched link 280 provides a similar function to that provided by the link 180 of the first alternative embodiment in that it joins adjacent gaps 240 to provide localized contraction to offset localized expansion caused by the tie bars 250 and allow the stent 210 as a whole to exhibit little if any contraction or expansion in the axial direction when radially expanded.

As an alternative to the strut 220, the arched links 280 can be replaced with links 180. Preferably in this embodiment, each flat trough 234 facing a gap 240 includes a tie bar 250 therein and each flat crest 236 adjacent a gap 240 including an arched link 280 attached thereto. Thus, no vacancies are provided in any of the flat troughs 234 or flat crests 236. In such a configuration, the stent 210 is provided with minimal flexibility for applications where radial strength is of primary importance and flexibility is of secondary importance. As an alternative, vacancies can be provided in the troughs 234 and the crests 236 in a manner similar to the preferred embodiment or the first alternative embodiment.

Figure 9:
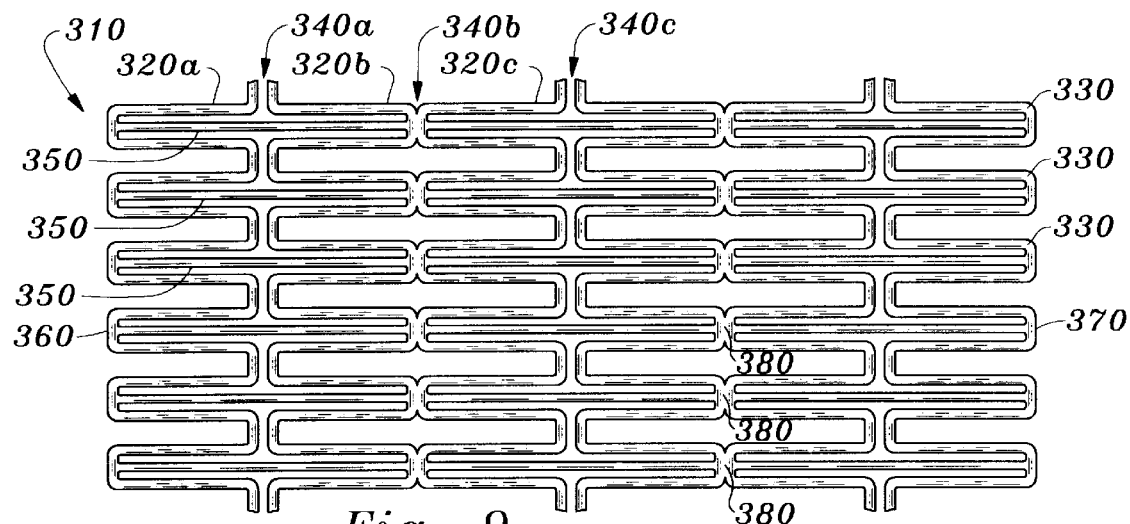
FIG. 9 is a top plan view of a stent forming a third alternative embodiment of that which is shown in FIG. 3, before radial expansion.
Figure 10:
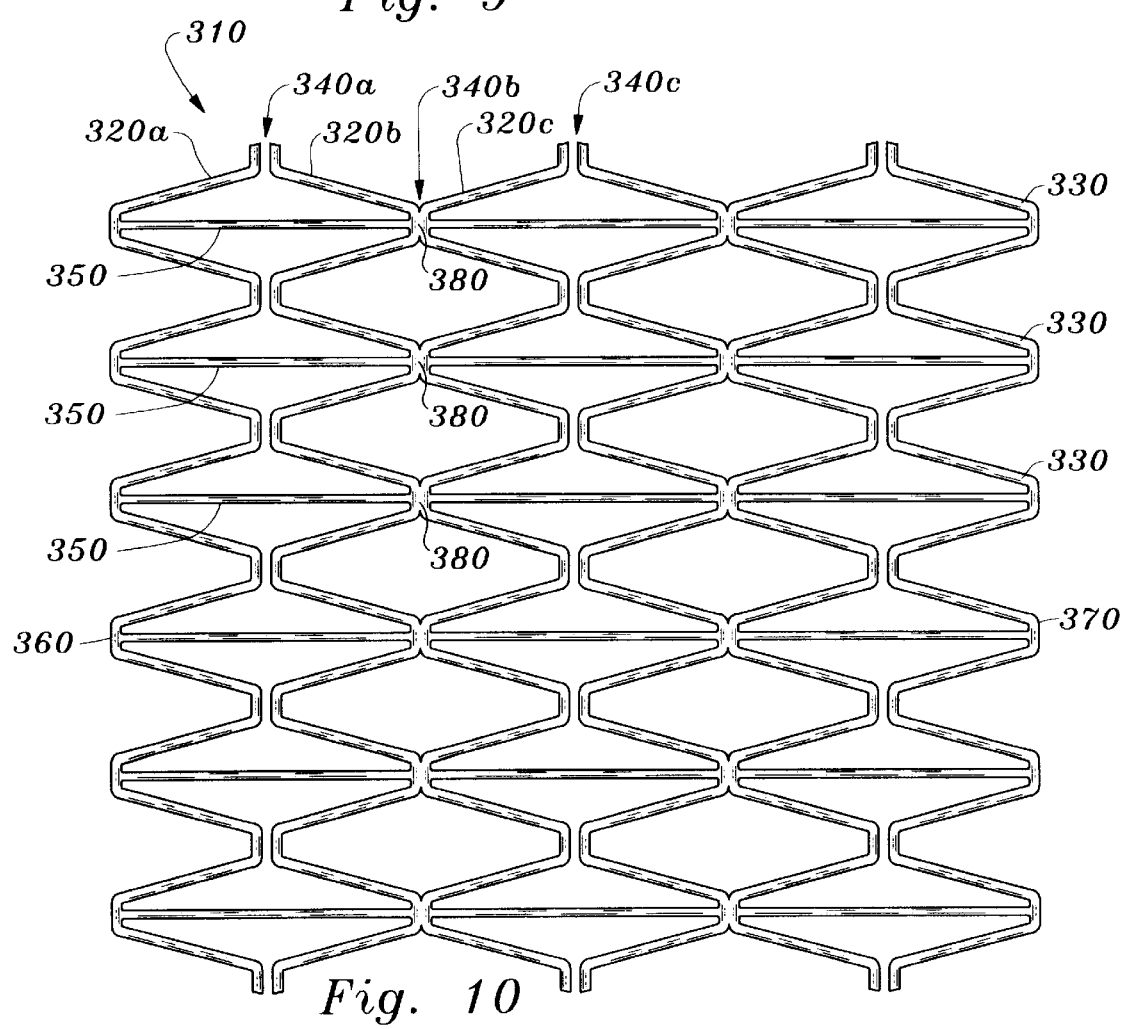
FIG. 10 is a top plan view of the stent which is shown in FIG. 9 after radial expansion has occurred.

With particular reference to FIGS. 9 and 10, details of a third alternative embodiment is provided of the surgical stent 10 of the preferred embodiment. This third alternative embodiment is for a stent 310 featuring multi-element junctions 380 therein. Details of the stent 310 are similar to those of the stent 210 except where particularly provided below. The stent 310 thus includes a series of struts 320 which circumscribe a cylindrical contour of the stent 310 and which exhibit a wave-like contour having bends 330. Gaps 340 are provided between adjacent struts 320. Alternating gaps 340, and particularly the gaps 340 adjacent the first end 360 and the second end 370 are fitted with tie bars 350 therein. Other gaps 340 can be fitted with either tie bars 350 or have a width thereof reduced to zero and have crests of struts 320 adjacent the gap 340 attached together at multi-element junctions 380.

In essence, the multi-element junction 380 replaces the arched link 280 of the second alternative embodiment and causes the gap 340 having multi-element junctions 380 therein to be reduced to a width of zero. The stent 310 is expandable in a manner similar to the stent 210. However, it is noted that because the tie bars 250 are aligned with the multi-element junctions 280, each of the individual tie bars 250 forms a continuous axial element extending from the first end 360 to the second end 370. Thus, an axial length of the stent 310 is maintained without contraction to a high degree of precision. The only possibility of axial contraction comes from any possible tie bar 350 bending, rather than the arrangement of the elements forming the stent 310. The tie bars 350 also provide a limited amount of flex for the stent 310. However, the stent 310 does not exhibit as much flexibility as the stents 10, 110, 210 of the other embodiments and is particularly suited for applications where flexibility is truly secondary and lack of axial contraction and radial strength are of primary importance.

Figure 11:
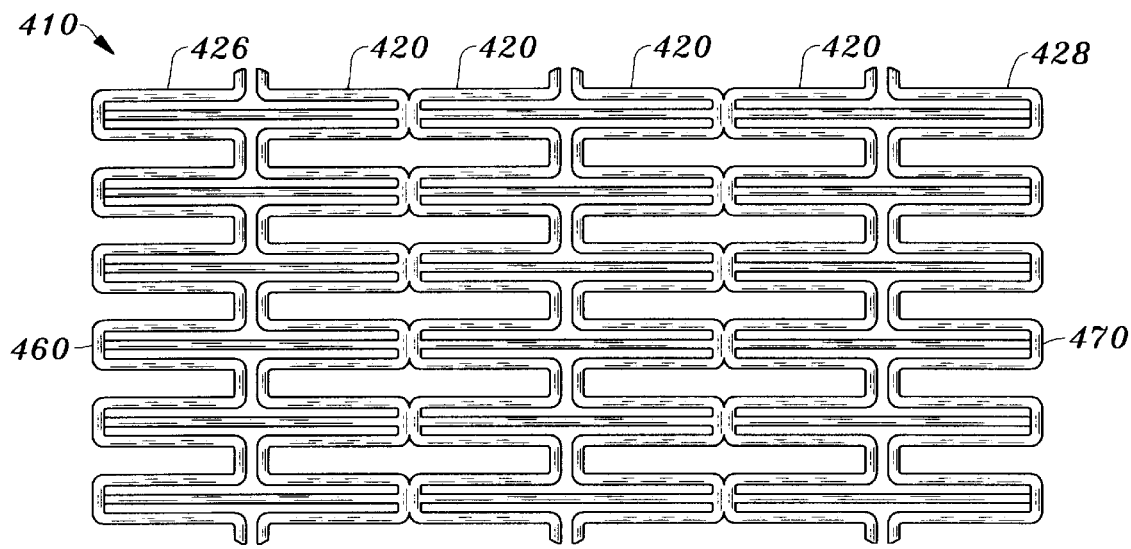
FIG. 11 is a top plan view of a stent forming an alternative embodiment to that which is shown in FIG. 9 with end struts thereof formed from a material having radio-opaque properties, before radial expansion.
Figure 12:
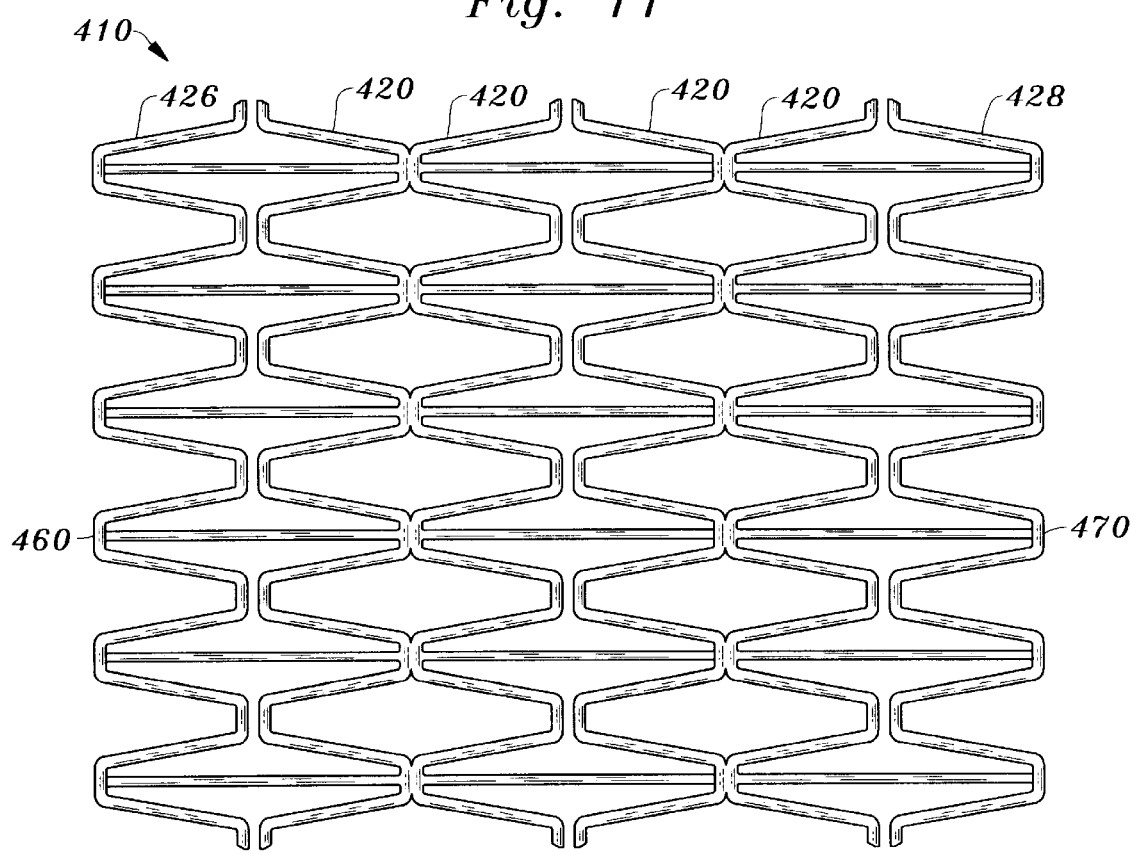
FIG. 12 is a top plan view of the stent which is shown in FIG. 11 after radial expansion thereof.

With particular reference to FIGS. 11, 12 and 13, details of a fourth alternative embodiment are provided. The stent 410 is only described to the extent that details thereof are distinct from details of the stent 310 of the third alternative embodiment. The stent 410 thus includes a series of struts 420 circumscribing the cylindrical contour of the stent 410. A first end strut 426 is located adjacent the first end 460 and a second end strut 428 is located adjacent the second end 470. These end struts 426, 428 are formed from a unique material from the material forming the middle struts 420 and other elements of the stent 410. This use of a different material than the material forming other elements of the stent 410 for the end struts 426, 428 could be similarly incorporated into the other stents 10, 110, 210, 310 of the other embodiments in a similar manner. The material forming the end struts 426, 428 is preferably a material exhibiting opacity when viewed by a medical imaging device to a greater extent than the material forming other portions of the stent 410. For instance, when stainless steel is utilized to form other portions of the stent 410, the end struts 426, 428 can be formed from a material such as gold, platinum, silver or some alloy or amalgam thereof, or other similar sufficiently dense material to provide a clear image when viewed by a medical imaging device.

The end struts 426, 428 are not namely plated with radio-opaque material. Rather the end struts 426, 428 are constructed out of the radio-opaque material. This is important because plating of stents, such as the stent 410, cause a thickness of elements forming the stents to be increased by a few thousandths of an inch. Such a plated stent then becomes difficult to maneuver through arterial pathways and other degradation in performance. Also, when end struts are thickened by plating, the radio-opaque material has a relatively broad profile that can be excessively bright when viewed with a fluoroscope or other medical imaging device, causing the stent's radio-opaque ends to appear blurry and not precisely defined. By forming the end struts 426, 428 entirely of radio-opaque material, the plating drawbacks are avoided.

As shown in FIG. 13, when the end struts 426, 428 are formed from a "radio-opaque" material, as described above, the ends 460, 470 of the stent 410 are clearly discernible when utilizing the medical imaging device. Additionally, the lumen L in which the stent 410 is located can be highlighted in a medical imaging device by coating the lumen L with a radio-opaque dye as is known in the art. A medical imaging device, such as an X-ray, can then be utilized to precisely determine the exact location of the stent 410 within the lumen L prior to or after expansion of the stent 410. Other portions of the stent 410 are either invisible when viewed with a medical imaging device or only vaguely discernible, as exhibited by FIG. 13 with broken lines. Preferably, the radio-opaque material forming the end struts 426, 428 is not merely a plating applied to the end struts 426, 428 but rather the end struts 426, 428 are formed entirely from the material selected.

In use and operation, and with particular reference to FIGS. 1, 2 and 13, details of the operation of the stents 10, 110, 210, 310, 410 are described. Initially, the stent 10 or alternative embodiment stents 110, 210, 310, 410 is provided in its non-radially expanded configuration as shown in FIG. 1. The stent is located at the desired position, utilizing prior art techniques such as catheterization, until the stent 10 is positioned where desired. The stent 10 is then expanded radially, along arrow R (FIG. 2), causing the wavelength 24 to increase, the amplitude 22 to decrease and the circumferential length (along arrow C of FIG. 2) to increase until the stent 10 is provided with the expanded diameter desired for the particular medical application. Because the stent 10 is configured as disclosed hereinabove and shown in the drawings, the first end 60 and second end 70 remain precisely positioned with respect to each other and with respect to the body lumen during the entire expansion process. Hence, little or no expansion or contraction of the stent 10 occurs.

When the stent 410 of the fourth alternative embodiment is utilized, the stent 410 is positioned as discussed above with respect to the preferred embodiment. However, before expansion of the stent 410 a radio-opaque dye is injected into the lumen involved and a medical imaging device, such as an X-ray machine, is utilized to verify that the stent 410 is positioned precisely where desired. If the position of the stent 410 is not precisely where desired, additional manipulation of the stent 410 can be done before expansion of the stent 410 has occurred. Once the medical professional is confident that the stent 410 is positioned where desired, the stent 410 is expanded as discussed above with respect to the preferred embodiment. Medical imaging devices can then be used immediately there after and on a follow-up basis to verify that the stent 410 is still in the desired position for maximum medical efficacy.

With particular reference to FIGS. 14–23, details of variations to the stent 110 (FIGS. 5 and 6) featuring links 180 as axial elements spanning gaps 140 of the stent 110 are described in detail. These different variations exemplify the range of configurations which the stent 110 can display for enhanced flexibility while maintaining the basic configuration of struts 120 spaced by gaps 140 with either tie bars 150 or links 180 spanning the gaps 140. A first enhanced flexibility stent 110a is shown in FIG. 14 which is similar to the stent 110 of FIGS. 5 and 6 except that three links 180 span each gap 140 where links 180 are located rather than only two links 180 as shown in the stent 110 of FIGS. 5 and 6. This enhanced flexibility stent 110a has a more radially symmetrical configuration than the stent 110 of FIGS. 5 and 6 so uniform flexibility is provided for the stent 110a.

Figure 5:
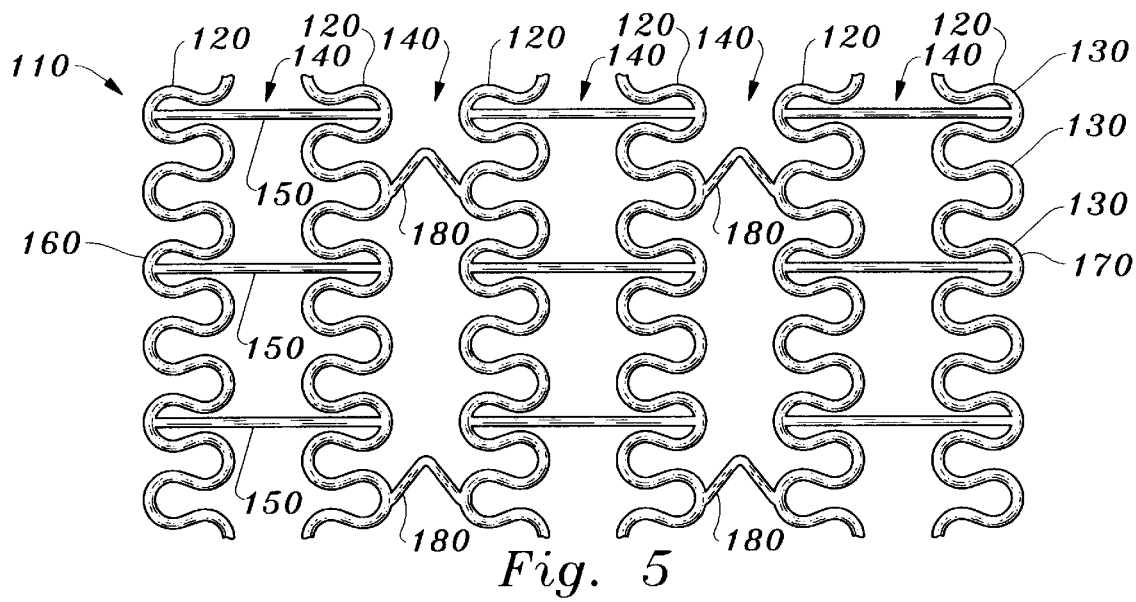
FIG. 5 is a top plan view of a stent forming a first alternative embodiment of that which is shown in FIG. 3, before radial expansion.
Figure 6:
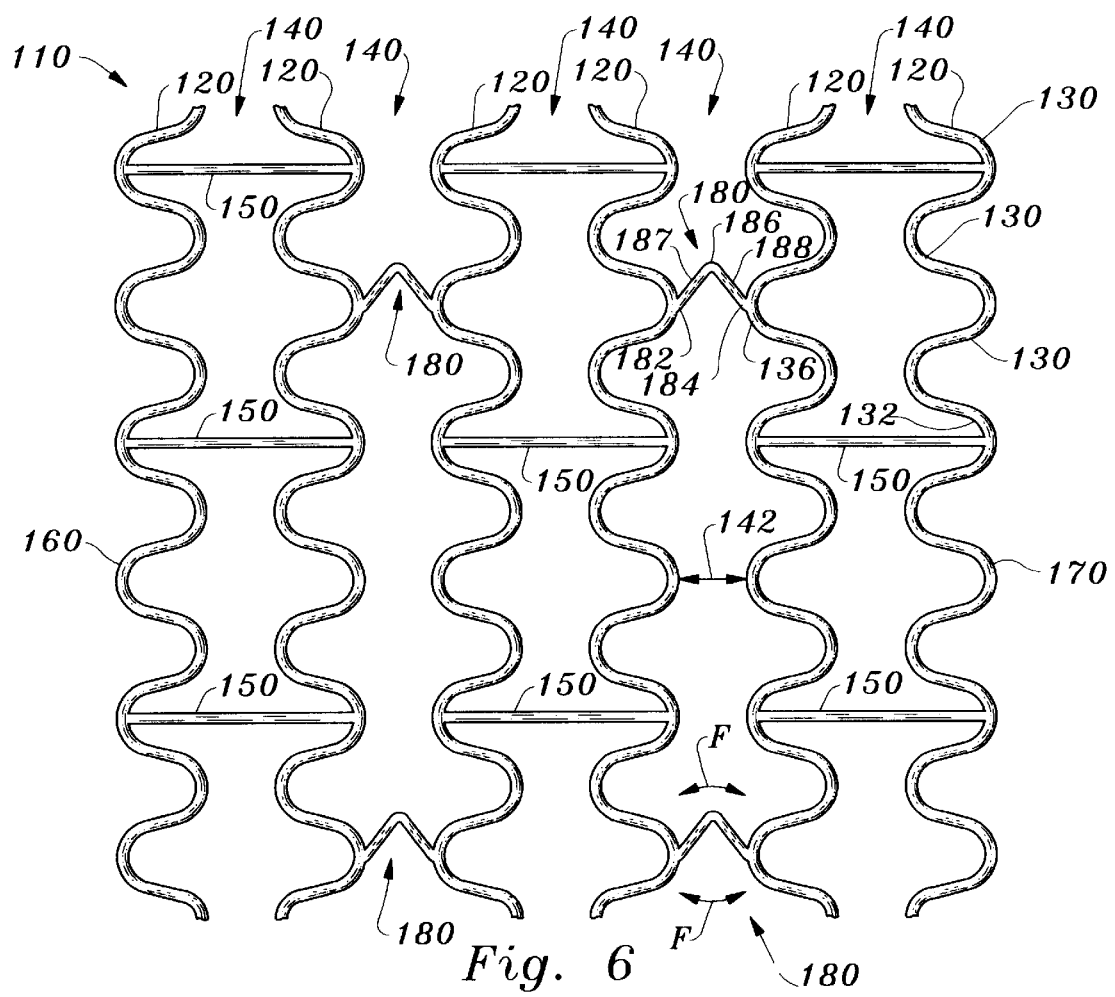
FIG. 6 is a top plan view of the stent which is shown in FIG. 5 after radial expansion has occurred.

The enhanced flexibility stent 110b of FIG. 15 similarly features a series of struts 120 spaced from each other by gaps 140 with either tie bars 150 or links 180 spanning each gap 140. The enhanced flexibility stent 110b (FIG. 15) differs from other enhanced flexibility stents 110, 110a described above in that each strut 120 includes ten bends 130 as the strut 120 circumscribes the stent 110b, rather than merely six bends 130 as shown in FIGS. 5, 6 and 14 for stents 110, 110a. Additionally, five tie bars 150 and five links 180 are provided within each gap 140. Additionally, extra struts 120, a total of sixteen, extend between the first end 160 and the second end 170 rather than fourteen struts 120 between the first end 160 and the second end 170 as shown in the enhanced flexibility stent 110a of FIG. 14.

The enhanced flexibility stent 110c is shown in FIG. 16. The stent 110c is similar to the enhanced flexibility stent 110b of FIG. 15 except that eight bends 130 are provided on each strut 120 and four tie bars 150 and four links 180 span each gap 140.

Figure 17:
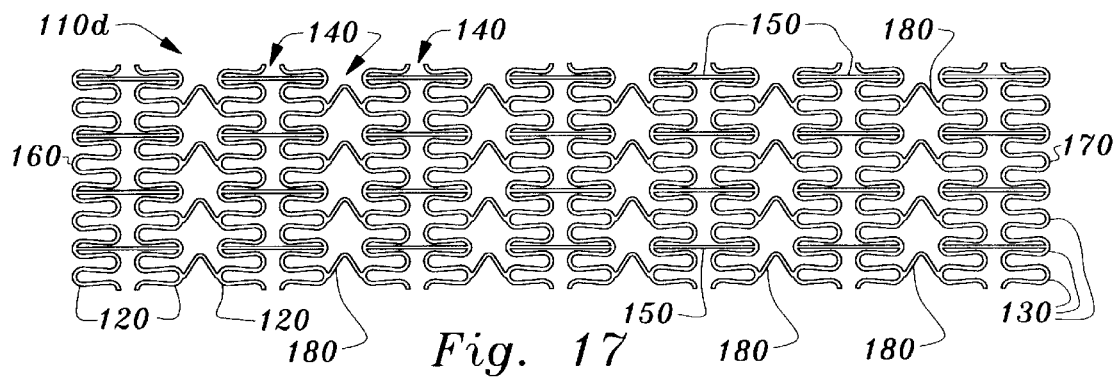
FIG. 17 is a cylindrical projection of an alternative to that which is shown in FIG. 16 where the struts exhibit a greater amplitude for a greater amount of radial expansion of the stent.

The enhanced flexibility stent 110d shown in FIG. 17 is similar to the enhanced flexibility stent 110c of FIG. 16 except that the struts 120 have a slightly different contour in the enhanced flexibility stent 110d than in the enhanced flexibility 110c of FIG. 16. Specifically, the struts 120 of the enhanced flexibility stent 110d have a larger amplitude (analogous to the amplitude 22 shown in FIG. 4) than an amplitude of the struts 120 of the other enhanced flexibility stents 110, 110a, 110b, 110c shown in FIGS. 5, 6 and 14–16. With a greater amplitude, the struts 120 can be radially expanded a greater amount, such that the enhanced flexibility stent 110d can experience a greater amount of radial expansion during implantation within a body lumen, as discussed above.

Figure 18:
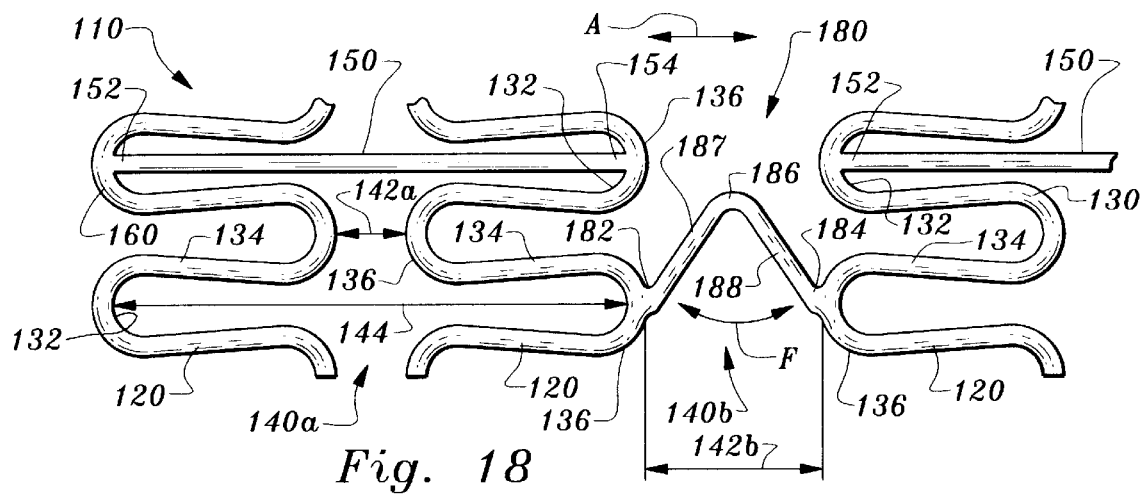
FIG. 18 is a cylindrical projection of a portion of that which is shown in FIG. 17 revealing details of the flexible axial linking elements of this invention.

With particular reference to FIG. 18, the specific features of individual components of the stent 110, which are also similarly shared by the stents 110a, 110b, 110c, 110d are shown in detail. Each strut 120 includes a series of bends 130 which alternative between troughs 132 and crests 136. Gaps 140 are provided between each strut 120. Each gap 140 is not the same. Rather, preferably the gaps 140 are divided into narrow gaps 140a and wide gaps 140b. The narrow gaps 140a are provided between struts 120 where a tie bar 150 is to be located. The wide gaps 140b are provided where the links 180 are provided. By making the gaps 140b wider than the gaps 140a and placing the links 180 within the wide gaps 140b, a greater amount of flexibility is allowed by the links 180 within the wide gaps 140b before struts 120 on opposite sides of the gaps 140b interfere with each other. Each gap 140a, 140b includes minimum widths 142a, 142b defining portions of the gaps 140a, 140b where a least spacing between adjacent struts 120 is provided. Each gap 140a, 140b also includes a maximum 144 where a maximum width is provided between adjacent struts 120.

Each tie bar 150 extends linearly and axially between a first junction 152 and a second junction 154. As discussed above, preferably both the first junction 152 and the second junction 154 are located within troughs 132 in each bend 130 such that the tie bars 150 span maximum width portions 144 of the narrow gaps 140a.

Figure 19:
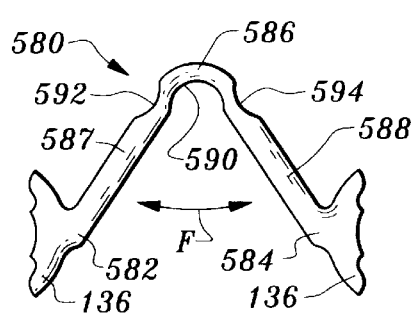
FIGS. 19–21 are cylindrical projections of a portion of that which is shown in FIG. 18 revealing three alternative embodiments for an elbow of the flexible axial linking element of the stent.
Figure 20:
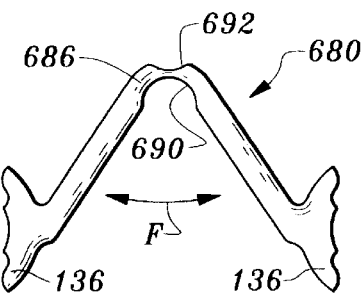
Figure 21:
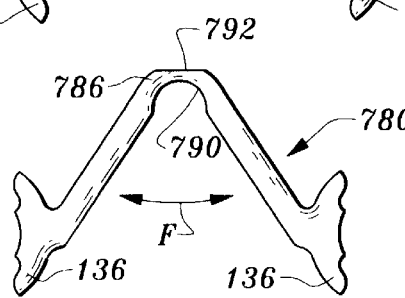

Each link 180 acts as an axial element which adds flexibility to the stent 110. In addition to the basic elements of the link 180 identified above with respect to FIGS. 5 and 6, the link 180 preferably features an elbow 186 which is configured with a means to flex, along arrow F, enhancing overall flexibility of the stent 110. Particularly, FIGS. 19–21 show three flex enhancement links 580, 680, 780 which reveal three alternative embodiments for enhancing the flexibility of the elbows 186 of the links 180 of the stent 110.

The first flex enhancement link 580 features a left end 582 adjacent one crest 136 and a right end 584 adjacent another crest 136. An elbow 586 is located between a left arm 587 extending from the left end 582 and a right arm 588 extending from the right end 584. Each arm 587, 588 extends linearly (when viewed in a two dimensional projection) from one of the ends 582, 584 to the elbow 586. In actuality, the arms 587, 588 curve slightly to follow the cylindrical contour of the stent 110 (see FIGS. 22 and 23).

The elbow 586 includes a bight 590 on an inside portion of the elbow 586 and a left depression 592 on an outside portion of the elbow 586 adjacent the left arm 587 and a right depression 594 on a portion of the elbow 586 adjacent the right arm 588. The elbow 586 has a width between the bight 590 and the left depression 592 and right depression 594 which is less than a thickness of the left arm 587 and the right arm 588.

This lessening in thickness can either be caused by forming the elbow 586 with this desired thinness initially or can be provided during a later step in the formation of the stent 110. For instance, when electropolishing or other polishing techniques are utilized, the elbow 586 being a point where a sharp bend occurs, provides a zone of concentrated charge where a greater amount of electropolishing occurs and which naturally results in the elbow 586 polishing down to a contour having a lesser thickness.

A second flex enhancement link 680 (FIG. 20) is similar to the first flex enhancement link 580 except that the elbow 686 of the second flex enhancement link 680 has an outside depression 592 opposite the bight 590 so that only a single narrow location in the elbow 686 is provided. The third flex enhancement link 780 (FIG. 21) is similar to the second flex enhancement link 680 except that the elbow 786 has a flat outside truncation 792 opposite the bight 590 to provide the elbow 786 with the desired thinness compared to the arms such as the arms 587, 588 of the first flex enhancement link 580, for facilitating flexing of the links 580, 680, 780 at the elbows 586, 686, 786.

If desired, the arms 187, 188 can be enlarged rather than reducing a thickness of the link 180 adjacent the elbow 186, so long as the elbow 186 has a lesser thickness than the arms 187, 188 of the link 180. Flexing of the link 180, along arrow F, is thus concentrated at the elbow 186. Flexing, along arrow F, can occur both in an elongating manner and in a shortening manner for the link 180, depending on whether tension or compression forces are applied to the link 180. In fact, when the stent 110 is bending (see FIGS. 22 and 23) each gap 140 having links 180 therein will have some links 180 on an inside curve of the stent 110 which are being compressed and other links 180 on the same gap 140 which are on the outside of the curve of the stent 110 and hence are being elongated.

Preferably, the elbows 186 of the links 180 do not elastically allow the arms 187, 188 to bend toward and away from each other, but rather flex in a plastic manner such that if unloaded after being flexed, the arms 187, 188 will retain the orientation which they exhibited when loaded with a compression or a tension load. However, when forces are again applied in an opposite direction, because the elbow 186 is a region of least thickness on the link 180, the elbow 186 will readily bend in an opposite direction allowing the link 180 to return to its original shape and to flex to other shapes as required to allow the stent 110 to flex. Such plastic flexing allows the stent 110 to hold a curve within a body lumen and not tend to try to straighten the body lumen in which the stent 110 is located.

To ensure that the plastic deformation of the links 180 and other portions of the stent 110 do not result in fracture of the stent 110, it is desireable that the stent 110 be heat treated to minimize brittleness for the stent 110. For instance, after manufacture of the stent 110, the stent 110 can be heated and then quenched as desired to produce a grain size consistent with the amount of flexibility and hardness which would give the stent the strength characteristics desired and yet avoid excessive brittleness.

With particular reference to FIGS. 22 and 23, details of the flexing characteristics of the enhanced flexibility stent 110*c* are shown in detail. In FIG. 22, the stent 110*c* is shown overlying a catheter J which includes a guide wire G and a balloon B surrounding the guide wire G. The catheter J and stent 110*c*are both flexed along a curve designated by arrow E. Each of the tie bars 150 and the struts 120 adjacent the tie bars 150 remains substantially axially aligned linearly without any flexing. However, gaps 140 (FIG. 17) which include the links 180 are altered so that portions of the gaps 140 are compressed and portions of the gaps 140 are expanded. Links 180 within the gaps 140 are either compressed to a lesser overall length or expanded to a greater overall length depending on whether the links 180 are on an inner side of the curve E or on an outer side of the curve E.

The guide wire G is utilized to lead the catheter J with the stent 110 thereon, down a desired arterial pathway for implantation. The balloon B can be blown up to radially expand the stent 110*c* to a desired final diameter. Because the stent 110*c* exhibits enhanced flexibility when compared to prior art stents, the stent 110*c* does not restrict an amount of flexibility the catheter J can exhibit. Rather, the stent 110*c* can freely flex along with the catheter J and follow the catheter J to whatever arterial pathway is desired for implantation of the stent 110*c*. The stent 110*c* is not merely restricted to curvature about a single axis. Rather, the stent 110*c* can flex helically or spirally as depicted in FIG. 23 and as is typically the case when navigating arterial pathways such as coronary arteries.

Figure 24:
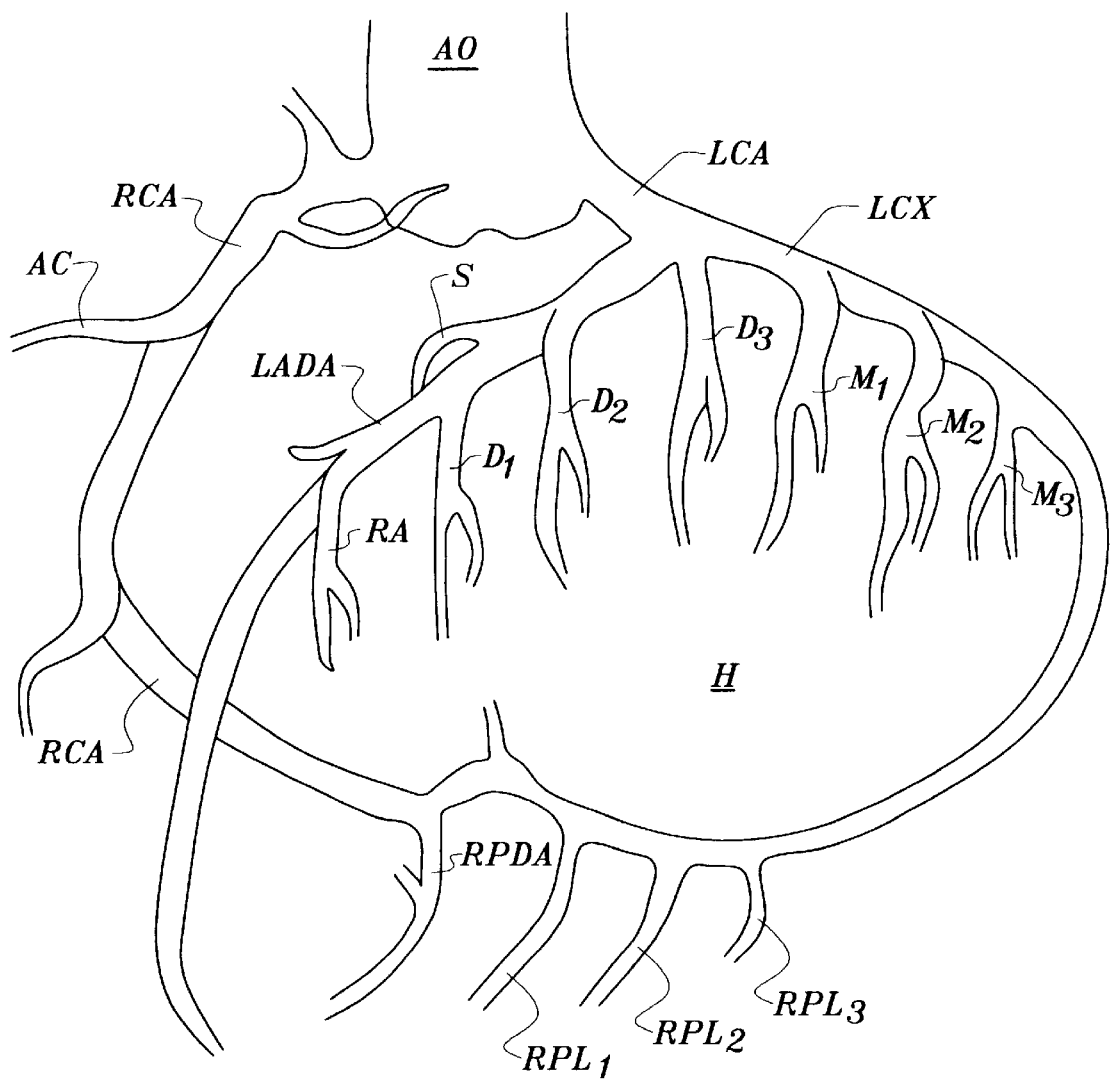
FIG. 24 is a schematic representation of arterial pathways of a heart which identifies some potential sites for implantation of the surgical stents of this invention.

With reference to FIG. 24, details of arterial pathways within a heart H in which implantation of an enhanced flexibility stent such as the stent 110*c* are described. The heart H is supplied with blood through a series of arterial pathways which branch off of the aorta AO and which together define arterial pathways for delivery of blood to the heart H. When lesions form in these arterial pathways, it is often desireable to locate radially expandable stents at a point of weakness and then radially expand these stents against the wall of the artery to support the wall of the artery adjacent the lesion so that blood flow through the artery can continue unimpeded.

While it is known to implant stents in primary arterial pathways such as the right coronary artery RCA, left coronary artery LCA, left circumflex artery LCX and left anterior descending artery LADA, certain secondary arterial pathways cannot be easily accessed with prior art stents. Rather, they require a stent with enhanced flexibility such as the stent 110*c* (FIG. 22).

Such secondary arterial pathways which can benefit from the implantation of an enhanced flexibility surgical stent 110*c* or other enhanced flexibility surgical stents 110, 110*a*, 110*b*, 110*d* include the AC marginal artery AC, right posterior lateral arteries $RPL_1$, $RPL_2$, $RPL_3$, the diagonal arteries $D_1$, $D_2$, $D_3$ of the left interior descending artery LADA along with the septal artery S and the ramus artery RA and the marginal arteries $M_1$, $M_2$, $M_3$ of the left circumflex artery LCX. These secondary arterial pathways are typically characterized in that they branch in a rather tortuous fashion off of primary arterial pathways and require a small diameter highly flexible stent for location and implantation therein. With enhanced flexibility stents 110, 110*a*, 110*b*, 110*c*, 110*d* tortuous pathways of lumens such as the secondary arterial pathways shown in FIG. 24 can be accessed and treated.

Moreover, having thus described the invention, it should be apparent that various different modifications could be made to the particular configuration of elements forming the stents 10, 110, 210, 310, 410 disclosed herein. For instance, while the different embodiments have featured different types and numbers of circumferential elements and axial elements, it is understood that many of these features could be utilized in other embodiments than those where such features are specifically shown. For instance, multi-element junctions such as the junctions 380 could be used to join together adjacent crests 36 of the struts 20 of the stent 10 of the preferred embodiment. Similarly, the stent 10 of the preferred embodiment could be provided with tie bars 50 located in every slot 46. The preferred embodiment and alternative embodiments described above are provided only by way of example and are not intended to restrict the scope of this invention as claimed.

What is claimed is:

1. An enhanced flexibility radially expandable substantially non-axially contracting surgical stent for implantation into a body lumen, such as an artery, said stent having a generally cylindrical contour both before and after radial expansion thereof, said stent comprising in combination:

at least three circumferential elements, each circumferential element forming an elongate circuit completely circumscribing said cylindrical contour;

each said circumferential element having a wave-like series of bends therein as each said circumferential element circumscribes said cylindrical contour of said stent;

each said wave-like series of bends including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

at least two gaps circumscribing said cylindrical contour of said stent between said at least three circumferential elements;

each one of said gaps having at least one axial element having two extremities and located spanning said gap between a pair of adjacent circumferential elements, said extremities each attached to a different one of said pair of adjacent circumferential elements, joining said pair of circumferential elements together;

at least one of said gaps spanned only by axial elements having each one of said extremities attached to an adjacent one of said circumferential elements at one of said troughs;

at least one of said gaps spanned by at least one axial element having a means to elongate axially when forces applied to said stent cause a central axis of said stent to bend, such that portions of said gap can elongate axially allowing said stent to bend; and wherein said gaps spanned only by axial elements having each said extremity attached at said troughs alternate with said gaps spanned by said axial elements having said means to elongate.

2. The enhanced flexibility stent of claim 1 wherein said axial elements which span said gaps with said extremities of said axial elements attached to said circumferential elements at said troughs are linear in form and aligned axially, parallel to said central axis of said stent.

3. The enhanced flexibility stent of claim 1 wherein said gaps include narrow gaps and wide gaps, said wide gaps having a greater width than said narrow gaps, said wide gaps alternating with said narrow gaps, said wide gaps having said axial elements having said means to elongate axially therein and said narrow gaps having said axial elements attached to said circumferential elements at said troughs therein.

4. An enhanced flexibility radially expandable substantially non-axially contracting surgical stent for implantation into a body lumen, such as an artery, said stent having a generally cylindrical contour both before and after radial expansion thereof, said stent comprising in combination:

at least three circumferential elements, each circumferential element forming an elongate circuit completely circumscribing said cylindrical contour;

each said circumferential element having a wave-like series of bends therein as each said circumferential element circumscribes said cylindrical contour of said stent;

each said wave-like series of bends including a trough and a crest, said trough defining a portion of said circumferential element where said circumferential element is more distant from adjacent said circumferential elements than other portions of said circumferential element, said crest defining a portion of said circumferential element where said circumferential element is closer to adjacent circumferential elements than other portions of said circumferential element;

at least two gaps circumscribing said cylindrical contour of said stent between said at least three circumferential elements;

each one of said gaps having at least one axial element having two extremities and located spanning said gap between a pair of adjacent circumferential elements, said extremities each attached to a different one of said pair of adjacent circumferential elements, joining said pair of circumferential elements together;

at least one of said gaps spanned only by axial elements having each one of said extremities attached to an adjacent one of said circumferential elements at one of said troughs;

at least one of said gaps spanned by at least one axial element having a means to elongate axially when forces applied to said stent cause a central axis of said stent to bend, such that portions of said gap can elongate axially allowing said stent to bend;

wherein said means to expand includes said axial element having a left arm attached to one of said circumferential elements at a left end and a right arm attached at a right end to an adjacent one of said circumferential elements, and an elbow attaching said left arm to said right arm, said elbow including means to flex; and wherein said left arm and said right arm are oriented non-parallel to each other and wherein said elbow is attached to said left arm at an end of said left arm opposite said left end, and said elbow attached to said right arm at an end of said right arm opposite said right end.

5. The enhanced flexibility stent of claim 4 wherein said means to flex of said elbow includes said elbow formed from a common material with said left arm and said right arm and having a width less than a width of said left arm and said right arm.

6. The enhanced flexibility stent of claim 5 wherein said elbow includes a bight on an inner side of said elbow and at least one depression on an outer side of said elbow, said elbow having lesser thickness between said depression and said bight than a thickness of said left arm and said right arm.

7. The enhanced flexibility stent of claim 6 wherein said elbow includes at least two depressions including a left depression at an end elbow adjacent said left arm and a right depression in said elbow on a portion of said elbow adjacent said right arm, said left depression and said right depression spaced from said bight by a width less than a width of said left arm and said right arm.

8. A surgical stent for implantation into a body lumen, said stent having a substantially cylindrical contour and being radially expandable, the stent comprising in combination:

a plurality of circumferential elements, each circumferential element encircling said cylindrical contour of said stent;

at least two of said plurality of circumferential elements having an undulating form including at least one trough and at least one crest as said undulating circumferential elements circumscribe said cylindrical contour of said stent;

at least one axial element located between two adjacent said circumferential elements and attached to one of said adjacent circumferential elements at a first junction and to the other of said circumferential elements at a second junction;

said at least one axial element having a means to elongate axially such that a central axis of said stent is allowed to bend;

wherein said at least one axial element includes a left end adjacent said first junction and a right end adjacent said second junction, said left end including a left arm extending from said left end, said right end including a right arm extending from said right end, and said left arm and said right arm coupled together at a medially located elbow there between, said elbow having a means to flex, such that said left end can be moved away from said right end and said axial element elongates; and wherein said left arm and said right arm extend linearly non-parallel to each other.

9. A surgical stent for implantation into a body lumen, said stent having a substantially cylindrical contour and being radially expandable, the stent comprising in combination:

a plurality of circumferential elements, each circumferential element encircling said cylindrical contour of said stent;

at least two of said plurality of circumferential elements having an undulating form including at least one trough and at least one crest as said undulating circumferential elements circumscribe said cylindrical contour of said stent;

at least one axial element located between two adjacent said circumferential elements and attached to one of said adjacent circumferential elements at a first junction and to the other of said circumferential elements at a second junction;

said at least one axial element having a means to elongate axially, such that a central axis of said stent is allowed to bend;

wherein said at least one axial element includes a left end adjacent said first junction and a right end adjacent said second junction, said left end including a left arm extending from said left end, said right end including a right arm extending from said right end, and said left arm and said right arm coupled together at an elbow there between, said elbow having a means to flex, such that said left end can be moved away from said right end and said axial element elongates; and wherein said means to flex includes said elbow having a thickness which is less than a thickness of said left arm and said right arm, said elbow having a sufficiently narrow thickness to allow said elbow to bend, such that said left arm and said right arm can be flexed toward and away from each other with said left end and said right end being drawn closer to and further away from each other.

10. A radially expandable surgical stent having a generally cylindrical contour, comprising in combination:

a plurality of circumferential elements circumscribing the cylindrical contour of said stent, said circumferential elements including means to radially expand;

at least one axial element between each adjacent pair of said circumferential elements; and at least one of said axial elements being an adjustable length axial element, said adjustable length axial element including:
a first arm attached to one circumferential element of the pair of circumferential elements at a first end;
a second arm attached to a second circumferential element of the pair of circumferential elements at a second end, said second arm not parallel with said first arm; and
a medially located elbow joining said first arm to said second arm, said elbow including means to flex causing said arms to pivot relative to each other and causing the pair of circumferential elements to move relative to each other.

11. The stent of claim 10 wherein said means to flex of said elbow includes said elbow having a lesser thickness than a thickness of said arms, such that said elbow exhibits a greater flexibility than said arms.

* * * * *